United States Patent [19]

Pader et al.

[11] 4,073,880
[45] Feb. 14, 1978

[54] ANTIPERSPIRANT SOLUTION CONTAINING A SUBSTANTIALLY VOLATILE POLYDIMETHYL SILOXANE LIQUID

[75] Inventors: Morton Pader, Teaneck; William Netzbandt, Dumont, both of N.J.

[73] Assignee: Lever Brothers Company, New York, N.Y.

[21] Appl. No.: 605,376

[22] Filed: Aug. 15, 1975

[51] Int. Cl.$^2$ ........................... A61K 7/34; A61K 7/38
[52] U.S. Cl. ......................................... 424/66; 424/68
[58] Field of Search ..................................... 424/68, 47

[56] References Cited

U.S. PATENT DOCUMENTS 3,018,223  1/1962  Siegal ....................................... 424/68

FOREIGN PATENT DOCUMENTS

| 779,899 | 2/1972 | Belgium | 424/47 |
| 2,035,901 | 12/1970 | France | 424/47 |
| 1,335,358 | 10/1973 | United Kingdom | 424/68 |

OTHER PUBLICATIONS

Todd et al., Amer. Perf. & Cosmetics, 1971, vol. 86, pp. 112–115.

*Primary Examiner*—Dale R. Ore
*Attorney, Agent, or Firm*—James J. Farrell; Melvin H. Kurtz; Kenneth F. Dusyn

[57] ABSTRACT

A formulation and method for a pump spray or roll-on antiperspirant is disclosed which antiperspirant is characterized by having superior drying properties. The formulation comprises one or more alcohol-soluble aluminum chlorhydroxide compounds in combination with an alcohol vehicle and a selected silicone liquid.

12 Claims, No Drawings

ANTIPERSPIRANT SOLUTION CONTAINING A SUBSTANTIALLY VOLATILE POLYDIMETHYL SILOXANE LIQUID

The present invention relates to liquid compositions which are particularly suitable for use in a pump spray or roll-on formulation.

Antiperspirant compositions have been manufactured in varying forms and such products as creams, lotions, roll-ons, gel sticks, and aqueous solutions to be applied by a pad, have been known for many years, for example, a liquid antiperspirant composition is disclosed in U.S. Pat. No. 2,955,983.

In more recent years a more convenient form of application of an antiperspirant has been developed. This is a pressurized antiperspirant system where the product is dispensed as a fine spray, as exemplified in U.S. Pat. No. 3,798,317. Several additional patents of interest in the antiperspirant art are as follows: U.S. Pat. Nos. 2,955,983; 3,359,169; 3,420,932; 3,509,253; 3,816,613; 3,863,005 and 3,873,686. Basically, the form of these aerosol products has developed as either a composition having an antiperspirant active agent suspended as a dry impalpable powder in a non-aqueous carrier vehicle or as a composition in which the active antiperspirant agent is dissolved in an alcoholic medium. Both of these compositions are dispensed from an aerosol container through a valve by the action of a propellant. The suspension of impalpable powder has achieved much greater use than the solution. One reason for this is that the suspension has proved to be much less corrosive to appropriately constructed cans. It is more important to consumer acceptance, however, that the product from the suspension in the propellant as it reaches the skin is in a form which contains little volatile material and therefore feels dry, comfortable, non-tacky and smooth. Alcoholic systems utilizing a solution rather than a suspension feel smooth and non-tacky when dry but are deposited in a wet tacky state. Nonetheless, the latter products, i.e. the alcoholic systems utilizing a solution enjoy a significant degree of consumer acceptance in the marketplace.

A major problem of aerosols in general, and of suspension products in particular, has been that as applied they cause a strong dusting and billowing of the spray, especially when the amount of carrier vehicle is reduced in order to minimize clothing staining potential of the formulation. In some instances, this dusting can be unpleasant to the user of the product and at best makes for less efficacious application of the product than is desirable.

Roll-on antiperspirants do not hasve some of the problems or pressurized aerosol sprays, however, these roll-on antiperspirants have their own specific drawbacks. These drawbacks are usually esthetic. In order words, a roll-on antiperspirant will normally be used by only one person because it comes in contact with the underarm and multiple usership is not desirable either esthetically or hygienically. Roll-on antiperspirants usually use a combination aqueous-alcohol solution of aluminum chlorhydroxide. Frequently these solutions during drying are very tacky to the touch. Also, the product takes a relatively long time to dry, and may leave an oily residue on the skin due to the oily material (lubricant) required to assure free functioning of the roll ball. Additionally, this lubricant also acts as an emollient. In addition to the roll-ons, cream antiperspirants are somewhat common but are also relatively messy to apply.

Because there are many problems related to aerosol antiperspirants, it becomes advantageous to investigate other methods of applying antiperspirant compositions which eliminate a propellant system and additionally eliminate the billowing problem which is attendant on the use of the finely divided aerosol pressurized sprays.

Accordingly, it is an object of the present invention to provide a pump spray or roll-on antiperspirant which can be applied in a manner which is relatively non-tacky and gives the perception of quick drying.

The attainment of the above object is made possible by this invention which includes a novel composition as well as a novel method for preparing pump spray or roll-on antiperspirants which are especially effective in that they deliver substantially non-tacky deposits of an alcohol soluble aluminum chlorhydrixde complex containing antiperspirant. The novel composition broadly comprises a solution in alcohol of Rehydrol* or other selected alcohol soluble aluminum chlorhydroxide compound or complex containing a selected cyclic poly alkyl siloxane compound which is essentially volatile.

*Rehydrol is the trademark used for an alcohol soluble aluminum chlorhydroxide complex marketed by Reheis Chemical Company.

The novel method comprises the addition of a selected cyclic poly alkyl siloxane compound to an alcohol solution of an alcohol soluble aluminum chlorhydroxide complex or compound to be used as a pump spray or roll-on antiperspirant solution to improve the drying characteristics of the composition. Thus, the composition, when applied to the skin is essentially non-tacky during drying and gives the sensation of fast drying.

Initially, formulations such as those used for roll-on antiperspirants, i.e. clear liquids, were investigated. It is recognized, however, that· such preparations which normally incorporate water dry very slowly on the skin and thus lead to an uncomfortable feel and consequently reduce the attractiveness of the product to the user. The problem of the rate of drying of these formulations is alleviated by using an essentially non-aqueous system, i.e. an alcohol. An aluminum chlorhydroxide propylene glycol complex marketed by the Reheis Chemcial Company under the trademark "Rehydrol" had been proposed for use in an aerosol composition. Several articles related to aerosol antiperspirants utilizing Rehydrol and in some cases small amounts of silicone have been published. Three of these articles are as follows: Parisse, American Perfumer and Cosmetics, Vol. 86 (1971) pages 46-48 and Todd in the same issue of the journal, pages 112-115; and "Aerosol Antiperspirants", reprinted in Soap Perfumery and Cosmetics, Vol. XL11 No. 2 February 1969, pages 723 and 724. These articles are directed to aerosol uses and do not consider pump spray or roll-ons. The main advantage of an alcohol-soluble source or aluminum chlorhydroxide is that a liquid substantially non-corrosive, markedly reduced billowing, non-dusting aerosol composition could be provided. This composition would not leave a dry powdery residue on the skin and would not leave a visible powdery dust in the atmosphere. Attempts were made to apply this development to an antiperspirant system which could be dispensed from a simple pump or roll-on. The advantages realized in the pump in terms of elimination of billowing or dusting plus an added advantage of economy, i.e. a maximal elimination of the property of powdered antiperspirants to bounce off the skin due to high pressure of application were accomplished by incorporating an alcohol soluble aluminum chlorhydroxide complex, alcohol and a selected cyclic poly alkyl silicone into a formulation to be dispensed by the pump mechanism. In addition, this formulation can also be used in a roll-on. Thus, pump spray and roll-on formulations were developed having Rehydrol in alcohol along with materials such as stearic acid, which inhibits the tendency to gel of alcoholic solutions of alcohol soluble aluminum chlorhydroxide, and a specified cyclic polydimethyl siloxane to reduce tackiness and provide a perception of quick drying.

The compositions of this invention are highly effective in adhering to the skin and in reducing or substantially eliminating the problems of antiperspirants dispensed in powdered forms, namely dusting and lack of good adhesion to the skin. Additionally, these compositions provide the advantage of substantially reducing the tackiness of alcohol solutions of the above-mentioned aluminum complexes. The subject invention encompassing novel compositions and novel processes overcomes one or more disadvantages of the prior art heretofore described. This is accomplished with the advantages described above.

The invention is hereinafter set forth in more detail, specific features thereof being particularly delineated in the appended claims.

More specifically, the compositions of this invention are represented by the following formulation:

| | Percent by Weight |
|---|---|
| alcohol soluble aluminum chlorhydroxide complex | about 5 to about 25 |
| alcohol | about 40 to about 85 |
| low molecular weight essentially volatile silicone (cyclic polydimethylsiloxane) | about 5 to about 40 |
| gel inhibitor | 0 to about 5 |
| optional antiperspirant agents | 0 to about 10 |
| adjuvants, e.g. lubricants, perfumes and the like | 0 to about 10 |

The alcohol soluble aluminum chlorhydroxide which is employed is preferably a propylene glycol complex or compound of aluminum chlorhydroxide. The preparation of this complex is described in U.S. Pat. No. 3,420,932. The preferred 1,2-propylene glycol derivative as described in the above-mentioned patent having the formula $Al_2(H_2O)_{0.7-1.1}(OH)_{4.9-5.1}(Cl)_{0.1-1.1}$ (1,2-propylene glycol)$_{0.7-1.3}$ is marketed as a powder under the Reheis Chemical Company trademark "Rehydrol". In essence, even through the above described propylene glycol derivative is preferred, any alcohol soluble form of aluminum chlorhydroxide may be utilized.

The amount of the complex employed is generally from about 5% to about 25% by weight of the composition and preferably from about 10% to about 20% by weight. A sufficient amount to provide antiperspirant activity must be used.

While the compositions are preferably substantially anhydrous some water content can be tolerated. The amount of water is determined by the solubility of the silicone in the total composition, but primarily in the alcohol/water phase. Typical solubilities have been reported by SWS Silicones to be as follows:

| % Water | % Ethyl Alcohol | % SWS-03314 (poly dimethylsiloxane) solubilized |
|---|---|---|
| 0 | 100 | soluble |
| 4 | 96 | 48 |
| 10 | 90 | 18 |
| 20 | 80 | 6 |
| 30 | 70 | 2 |
| 35 | 65 | less than 1 |

From these solubilities it is clear that the composition cannot tolerate more than about 20% water and preferably will be much less viz. essentially anhydrous. It must be realized in this regard that lubricants as well as other adjuvants are also relatively water intolerant.

The alcohol used in preferably essentially anhydrous ethanol and denatured ethanol meeting this criteria, which is also cosmetically acceptable is, of course, appropriate. Other short chain cosmetically acceptable alcohols such as for example isopropanol may also be utilized but the characteristic odor makes these other alcohols less desirable. The amount of alcohol required is from about 40 to about 85% by weight of the total composition, preferably from about 60 to 80% by weight. The lower limit is dictated by the requirement of solubility of the other components of the mixture. If less than about 40% is used, difficulty is encountered in dissolving the other components and in attaining a solution of the proper flow characteristics for pump spray or roll-ball action. If more than about 85% is used, the amount of the other components is too low to effectively perform their functions. 65 to 80% represents the most preferable range to achieve good solubility together with acceptable efficacy. Generally, for either a pump spray or roll-on deodorant composition a viscosity which is capable of being aspirated in a pump spray or capable of being free flowing without clogging the ball applicator on a roll-on is required; the preferred viscosities are well known in the art.

The gel inhibiting agent is used to prevent gelling of the composition over extended storage periods especially at elevated temperatures. A practical commercial product thus will of necessity include a gel inhibiting agent. However, the invention lies in the provision of a component which renders the alcohol soluble complexes less tacky on drying and thus the combination of alcohol, alcohol soluble aluminum chlorhydroxide complex and cyclic polydimethyl siloxane will be completely effective for its intended purpose, in some cases for months, without the inclusion of a gel inhibitor. As previously stated, however, a commercial product must have a long storage life and may be exposed to high temperatures and therefore will require gel inhibition. Gel inhibitors known to the art may be used. Triple pressed stearic acid, which is a combination of about 50% by weight stearic acid with about 50% by weight myristic acid, has been found to be preferable to satisfactorily inhibit gelling of the composition. Any gel inhibitor that performs satisfactorily may also be used, such as for example, isostearic acid, propylene glycol, oleyl alcohol, hexadecyl alcohol, and the like and combinations and mixtures thereof. The amount of gel inhibiting agent when used in from about 0.5% by weight to about 5% by weight of the total composition and preferably from about 1% to about 3.5%. Higher amounts provide no additional benefits. The lower limits are dictated by a sufficient amount to prevent gelling of a commercial composition. From about 1 to 3.5% is particularly effective to achieve a free flowing composition.

Optional antiperspirant agents that may be used are aluminum chloride, zirconyl oxychloride and basic aluminum bromide as well as other agents known in the art, see for example U.S. Pat. No. 2,906,668. The use of these agents will, of course, depend on their compatibility in the system, which compatibility can be evaluated by simple empirical methods.

Adjuvants that may be used are skin lubricants such as isopropyl myristate, propylene glycolmonoisostearate, isopropyl palmitate, ethoxylated lanolin, and the like. Perfume is also optionally added. These adjuvants must be compatible with the other components of the system and must not leave a residue which substantially interferes with efficacy. The choice of adjuvants is within the knowledge of one skilled in the art and since the adjuvants are not critical to the invention, no exhaustive listing will be made. Generally, these adjuvants or additives, when present, ar included in an amount up to about 10% by weight of the composition.

A cyclic polydimethylsiloxane of the formula

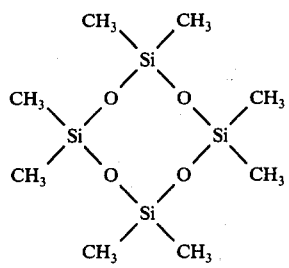

is the low molecular weight volatile silicone of this invention. As prepared commercially, this compound may contain small amounts of the less volatile corresponding 10 membered ring structure. This 10 membered compound, while less volatile than the 8 membered compound shown, does not interfere with the functioning of the 8 membered ring structure and has utility in itself. This cyclic 8 membered ring polydimethyl siloxane is relatively volatile and has been found to reduce or substantially eliminate tackiness of the composition when added in the proportions cited above, as well as to enhance the perception of fast drying.

The dimethylsiloxane is available, for example, under the designation Volatile Silicone 7207 from Union Carbide Corporation or Siloxane SWS-03314 or 03400 from SWS Silicones, a division of Stouffer Chemcial Company. These silicones can be characterized generally for example by the following constants, given by the manufacturer, for SWS-03400: Specific Gravity 0.960 at 25° C; viscosity about 5 centistokes at 25° C and 98% volatile components.

This volatile siloxane is employed in an amount of about 5% to about 40% by weight of the total composition, preferably from about 10% to about 20% by weight. If a substantial excess above 40% is used, it leads to problems of insolubility of either the silicone or of other components due to the reduced alcohol level and a high incidence of gelling of the composition. In addition to the technical problems raised, higher amounts are uneconomical. If the amount used is less than 5%, the silicone does not adequately fulfill its function. Particularly effective levels of silicone to avoid undue gelation and tackiness are from about 10% to about 20% by weight.

The polydimethylsiloxane, being relatively volatile, may tend to evaporate between uses from the orifice of the pump spray valve, and thus, in some pump valve construction leave a powdery residue which may interfere with the next actuation of the pump. This can be overcome by rinsing the valve, selecting a valve which eliminates streaming so that only minor amounts of residue are present at the orifice at any time or by adding a lubricant which inhibits formation of a powdery residue at the orifice. In the case of a roll-ball the above problems are evident in sticking of the roll-ball; a lubricant will also overcome this problem.

As mentioned above, in addition to pump spray antiperspirants, the instant composition may be used as a roll-on deodorant either with or without incorporating a thickening agent to achieve the proper viscosity for application. If it is desirable to use a thickening agent, then any compatible thickening agent may be used in an amount sufficient to thicken the composition. A hydroxypropyl cellulose thickener, such as Klucel Type G marketed by Hercules Powder Corporation, having a typical molecular weight of 300,000 may be used. The viscosity of a 2% solution of this hydroxypropyl cellulose in ethanol will range from about 75 to 400 centipoise at 25° C.

The following Examples will more fully illustrate the embodiments of this invention. All parts and proportions referred to herein and in the appended claims are by weight unless otherwise indicated.

EXAMPLE I

A number of compositions are prepared utilizing Rehydrol by dissolving the Rehydrol in ethanol and then adding the other components. Sufficient Rehydrol is added, with stirring at ambient temperatures, to ethanol to result in a 30% be weight solution of Rehydrol. The balance of the alcohol is then added with stirring. The triple pressed stearic acid gel inhibitor (all stearic acid in the Examples is triple pressed and is an approximately 50% by weight mixture of stearic and myristic acids) is then stirred into the Rehydrol solution. The balance of the ingredients are then added with stirring to form a solution. The solution is then introduced into the desired applicator and tested.

The compositions prepared in the above manner together with results are presented in tabular form.

TABLE 1

| | CONTROL EXAMPLES | | | |
|---|---|---|---|---|
| | 1 | 2 | 3 | 4 |
| | % % | % | % | |
| Rehydrol | 10.0 | 15.0 | 20.0 | 15.0 |
| Stearic Acid | 1.0 | 1.5 | 1.5 | — |
| Isopropyl myristate | 1.0 | 1.0 | 1.0 | 1.0 |
| Alcohol (ethanol) | 87.5 | 82.0 | 77.0 | 83.5 |
| Perfume | 0.5 | 0.5 | 0.5 | 0.5 |
| | 100.0 | 100.0 | 100.0 | 100.0 |

Each of the Formulas 1 through 4 produce an objectionable sticky feel during drying. Formula 4, containing no gel inhibitor, gels on extended aging.

TABLE 2

Comparative    Comparative

TABLE 2-continued

|  | 5 | 6 |
|---|---|---|
|  | % | % |
| Rehydrol | 10.0 | 15.0 |
| Stearic acid | 1.0 | 3.5 |
| Isopropyl myristate | 1.0 | 1.0 |
| Perfume | 0.5 | 0.5 |
| Ethanol | 77.7 | 74.0 |
| Trichlorotrifluoro-ethane (Freon 113) | 9.8 | — |
| Glycerine | — | 6.0 |
|  | 100.0 | 100.0 |

Formula 5, utilizing Freon 113 as a spray assist, produces a stinging sensation and is sticky during drying.
Formula 6, employing no silicone but utilizing glycerin as a lubricant, feels very sticky during drying.

|  | 7 | 8 | 9 | 10 | 11 | 12 | 13 | 14 | 15 | 16 |
|---|---|---|---|---|---|---|---|---|---|---|
|  | % | % | % | % | % | % | % | % | % | % |
| Rehydrol | 15.0 | 15.0 | 15.0 | 20.0 | 15.0 | 15.0 | 10.0 | 15.0 | 15.0 | 15.0 |
| Isopropyl myristate | 1.0 | 1.0 | 1.0 | 1.0 | 1.0 | 1.0 | 1.0 | 1.0 | 1.0 | — |
| Stearic acid | 1.5 | 3.5 | — | 3.5 | 1.5 | 1.5 | 1.5 | 2.0 | 3.5 | 1.5 |
| Volatile Silicone 7207 | 15.0 | 15.0 | 15.0 | 15.0 | 20.0 | 10.0 | 5.0 | 30.0 | 40.0 | 15.0 |
| Perfume | 0.5 | 0.5 | 0.5 | 0.5 | 0.5 | 0.5 | 0.5 | 0.5 | 0.5 | 0.5 |
| Ethanol | 67.0 | 65.0 | 68.5 | 60.0 | 62.0 | 72.0 | 82.0 | 51.5 | 40.0 | 67.0 |
|  | 100.0 | 100.0 | 100.0 | 100.0 | 100.0 | 100.0 | 100.0 | 100.0 | 100.0 | 100.0 |

Formula 7 very satisfactory, non-sticky, leaves skin dry, dries fast
Formula 8 very satisfactory, non-sticky, leaves skin dry, dries fast
Formula 9 non-sticky, but since it does not include a gel inhibitor, it gels on extended aging.
Formula 10 satisfactory
Formula 11 satisfactory, very slightly drier than 9
Formula 12 satisfactory
Formula 13, using low levels of Rehydrol and silicone, is acceptable
Formula 14, utilizing a relatively high level of silicone, gave good results
Formula 15, using a very high level of silicone, gave good results
Formula 16, using no skin lubricant, gave good results

|  | 17 | 18 | 19 | 20 | 21 | 22 | 23 | 24 |
|---|---|---|---|---|---|---|---|---|
|  | % | % | % | % | % | % | % | % |
| Rehydrol | 15.0 | 15.0 | 15.0 | 15.0 | 14.0 | 10.0 | 15.0 | 15.0 |
| Stearic Acid | 1.5 | — | — | — | 1.5 | 1.5 | — | — |
| Isostearic Acid | — | 1.5 | — | — | — | — | — | — |
| Hexadecyl Alcohol | — | — | 3.0 | — | — | — | — | — |
| Crodafas N10 Acid* | — | — | — | 3.0 | — | — | — | — |
| Oleyl Alcohol | — | — | — | 1.0 | — | — | — | — |
| Isopropyl Myristate | — | 1.0 | 1.0 | — | 1.0 | 1.0 | — | — |
| Volatile Silicone 7207 | 15.0 | 15.0 | 15.0 | 15.0 | 10.0 | 10.0 | 20.0 | 10.0 |
| Aluminum Chloride | — | — | — | — | 1.0 | — | — | — |
| Zirconium Oxychloride | — | — | — | — | — | 1.0 | — | — |
| Ethanol | 68.0 | 67.0 | 65.5 | 65.5 | 72.0 | 76.0 | 64.5 | 74.5 |
| Perfume | 0.5 | 0.5 | 0.5 | 0.5 | 0.5 | 0.5 | 0.5 | 0.5 |
|  | 100.0 | 100.0 | 100.0 | 100.0 | 100.0 | 100.0 | 100.0 | 100.0 |

*oleyl ether phosphate marketed by Croda Inc.
Formulas 17 through 20 inclusive varied the gel inhibitor and all four produced acceptable results.
Formulas 21 and 22 vary the active component, both formulations produce acceptable results.
Formulas 23 and 24 containing no gel inhibitor, give acceptable results and are stable for at least three months at room temperature and 105° F.

|  | 25 | 26 | 27 |
|---|---|---|---|
|  | % | % | % |
| Chlorhydrol (aluminum chlorhydroxide) | 20.0 | 15.0 | — |
| Rehydrol | — | — | 15.0 |
| Stearic acid | — | — | 1.5 |
| Solulan 98* | 2.0 | 2.0 | — |
| Isopropyl myristate | — | — | 1.0 |
| Siloxane 03314 | 0 | 1 | 15.0 |
| Perfume | 0.5 | 0.5 | 0.5 |
| Water | 47.5 | 32.5 | — |
| Klucel Type G (hydroxypropyl cellulose) | — | — | 0.7 |
| Ethanol | 30.0 | 50.0 | 65.3 |
|  | 100.0 | 100.0 | 100.0 |

|  | 28 |
|---|---|
|  | % |
| Alcohol soluble aluminum chlorhydrate | 15.0 |
| Stearic acid | 1.5 |
| Isopropyl myristate | 1.0 |
| Volatile Silicone 7207 | 15.0 |
| Perfume | 0.5 |
| Ethanol | 67.0 |
|  | 100.0 |

Formulas 25 and 26, using chlorhydrol and water, are very sticky and slow drying.
Formula 27 is a thickened composition suitable for a roll-on.
Formula 28, utilizing an alcohol soluble aluminum chlorhydrate other than Rehydrol, gave good results.
*an ethoxylated lanolin alcohol marketed by Amerchol, a division of C.P.C.

Generally, the Examples show that a pump spray formulation comprising an alcoholic solution of an alcohol soluble aluminum chlorhydroxide such as Rehydrol is rendered much less tacky during drying by the utilization of the polydimethylsiloxane of this invention. The tack is measured either by subjective tactile analysis or by a compound lever assembly attached to an Instron machine which measures the tack of a particular composition in a graphical manner. The Instron test assembly generally measures the force required to separate test surfaces. The formulation is spread on one surface and the a second surface is brought into contact with the first surface. As the Instron crosshead moves, the surfaces are separated. If the formulation is tacky during drying, an increase in the force necessary to separate the surfaces is observed.

In addition to individual laboratory personnel measuring tack, the tack is also measured by the use of consumer panels. In such tests it is found that users appreciate the decrease in tackiness resulting from the use of the volatile silicone of this invention. The consumer acceptability of the formulations exemplified in this invention is tested and an acceptable rating indicates consumer acceptability.

The comparative Examples used show the distinction between the formulations of this invention is comparison with both control examples and several examples utilizing water solutions, a spray assisting additive and some common lubricants.

This invention has been described with respect to certain preferred embodiments, and various modifications and variations in the light thereof will be suggested to persons skilled in the art and are to be included within the spirit and purview of this application and the scope of the appended claims.

What is claimed is:

1. An antiperspirant solution suitable for pump spray or roll-on application consisting essentially of an alcohol soluble aluminum chlorhydroxide complex; a sufficient amount of a polydimethyl siloxane of the structural formula

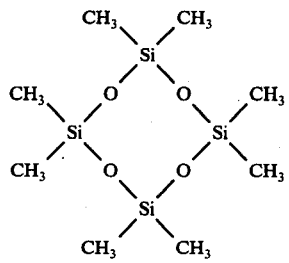

to substantially reduce the tackiness of said complex during drying; and a sufficient amount of alcohol to result in said solution; said composition being characterized by having substantially reduced tackiness and giving a preception of quick drying when applied from a pump spray or a roll-on applicator.

2. An antiperspirant solution as defined in claim 1 having a gel inhibitor incorporated into said solution in an amount sufficient to substantially reduce gelling thereof upon extended aging.

3. An antiperspirant solution as defined in claim 2 wherein said gel inhibitor is selected from the group consisting of triple pressed stearic acid, isostearic acid, hexadecyl alcohol, oleyl alcohol and mixtures thereof.

4. An antiperspirant solution as defined in claim 1 wherein said complex is a 1,2-propylene glycol complex of aluminum chlorhydroxide present in an amount of about 5% to about 25% by weight of said solution.

5. An antiperspirant solution as defined in claim 4 wherein said complex has the formula: $Al_2(H_2O)_{0.7-1.1}(OH)_{4.9-5.1}(Cl)_{0.1-1.1}(1,2\text{-propylene glycol})_{0.7-1.3}$ 6. An antiperspirant solution as defined in claim 1 consisting of:
   a. about 5 to about 25% by weight of an alcohol soluble aluminum chlorhydroxide complex;
   b. about 40 to about 85% by weight of ethanol;
   c. about 5 to about 40% by weight of polydimethylsiloxane of the structural formula

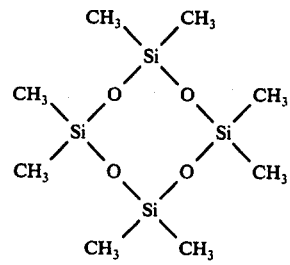

d. about 0.5 to about 5% by weight of a gel inhibitor;
   e. up to about 10% of an optional antiperspirant agent selected from the group consisting of aluminum chloride, zirconium oxychloride, basic aluminum bromide and mixtures thereof; and
   f. up to about 10% of adjuvants.

7. An antiperspirant solution as defined in claim 6 wherein said complex is a 1,2-propylene glycol complex of aluminum chlorhydroxide.

8. An antiperspirant solution as defined in claim 6 wherein said gel inhibitor is selected from the group consisting of triple pressed stearic acid, isostearic acid, hexadecyl alcohol, oleyl alcohol and mixtures thereof.

9. An antiperspirant solution as defined in claim 1 consisting of:
   a. 15% by weight of an aluminum chlorhydroxide complex having the formula $Al_2(H_2O)_{0.7-1.1}(OH)_{4.9-5.1}(Cl)_{0.1-1.1}(1,2\text{-propylene glycol})_{0.7-1.3}$,
   b. 1.5% by weight of triple pressed stearic acid;
   c. 1.0% by weight of isopropyl myristate;
   d. 15% by weight of polydimethylsiloxane of the structural formula

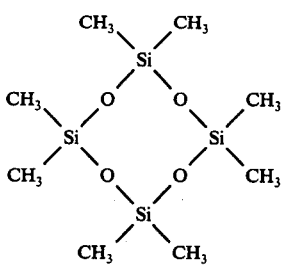

e. 0.5% by weight of perfume; and
   f. 67% by weight ethanol.

10. An article of manufacture comprising a solution as defined in claim 1 disposed in a pump spray applicator.

11. An article of manufacture comprising a solution as defined in claim 1 disposed in a roll-on applicator.

12. A method for substantially reducing the tackiness during drying and giving the perception of being quick drying of an alcohol solution of an alcohol soluble aluminum chlorhydroxide complex comprising introducing into said solution a sufficient amount of a polydimethyl siloxane of the structural formula

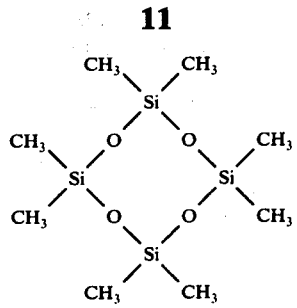
to result in said substantial reduction of tackiness, and said perception of quick drying.
* * * * *